(12) United States Patent
Shuk et al.

(10) Patent No.: US 10,161,899 B2
(45) Date of Patent: Dec. 25, 2018

(54) OXYGEN SENSOR WITH ELECTROCHEMICAL PROTECTION MODE

(71) Applicant: Rosemount Inc., Shakopee, MN (US)

(72) Inventors: Pavel Shuk, Copley, OH (US); Robert F. Jantz, Tustin, CA (US)

(73) Assignee: Rosemount Inc., Shakopee, MN (US)

( * ) Notice: Subject to any disclaimer, the term of this patent is extended or adjusted under 35 U.S.C. 154(b) by 570 days.

(21) Appl. No.: 14/502,490

(22) Filed: Sep. 30, 2014

(65) Prior Publication Data

US 2016/0091458 A1 Mar. 31, 2016

(51) Int. Cl.
*G01N 27/407* (2006.01)
*G01N 27/406* (2006.01)

(52) U.S. Cl.
CPC ....... *G01N 27/4065* (2013.01); *G01N 27/407* (2013.01)

(58) Field of Classification Search
CPC ..................................... G01N 27/406–27/4118
USPC ...................... 204/421–429; 205/783.5–786; 73/23.31–23.33
See application file for complete search history.

(56) References Cited

U.S. PATENT DOCUMENTS

| | | | |
|---|---|---|---|
| 3,928,161 A | 12/1975 | McIntyre et al. | |
| 4,158,166 A * | 6/1979 | Isenberg | F23N 5/006 204/426 |
| 4,266,519 A | 5/1981 | Norimatsu et al. | |
| 4,294,668 A * | 10/1981 | Young | G01N 27/4075 204/424 |
| 4,391,251 A * | 7/1983 | Planteline | F02D 41/26 123/687 |
| 4,543,176 A * | 9/1985 | Harada | G01N 27/4067 204/406 |
| 4,702,971 A | 10/1987 | Isenberg | |
| 5,980,728 A | 11/1999 | Farber et al. | |
| 6,165,336 A * | 12/2000 | Maki | G01N 27/4074 204/415 |
| 7,527,717 B2 | 5/2009 | Shuk et al. | |
| 7,630,840 B2 | 12/2009 | Sell et al. | |
| 2013/0233728 A1 | 9/2013 | Day et al. | |

OTHER PUBLICATIONS

"The CRC Handbook of Solid State Electrochemistry", by P. J. Gellings and H. J. M, Bouwmeester,618 pages, CRC Press, Boca Raton (1997).
"Process Zirconia Oxygen Analyzer: State of Art", by P. Shuk, Technisches Messen, pp. 19-23, (2010).

(Continued)

*Primary Examiner* — Bach T Dinh
(74) *Attorney, Agent, or Firm* — Christopher R. Christenson; Kelly, Holt & Christenson PLLC

(57) ABSTRACT

A process analytic instrument includes a measurement cell and an analyzer circuit. The measurement cell includes a solid state electrochemical oxygen sensor configured for exposure to a process gas. The analyzer circuit is coupled to the solid state electrochemical sensor to measure an electrical parameter of the solid state electrochemical sensor and provide an output indicative of oxygen in the process gas. A DC bias circuit is configured to selectably bias the solid state electrochemical oxygen sensor with a direct current when the solid state electrochemical sensor is in a reducing environment.

17 Claims, 4 Drawing Sheets

(56) References Cited

OTHER PUBLICATIONS

"Handbook of Zeolite Science and Technology", by S. M. Auerbach, K. A. Carrado, P. K. Dutta, 1283 pages, Marcel Dekker, New York (2003).
International Search Report and Written Opinion for International Application No. PCT/US2015/051255, dated Jan. 27, 2016, date of filing: Sep. 21, 2015, 13 pages.
T.F Kearns: "Electrochemical protection against high-temperature oxidation", IDA paper P-2093 IDA log No. HQ 88-30190, 42 pp. (1988).
International Preliminary Report on Patentability for PCT/US2015/051255, dated Apr. 13, 2017, 12 pages.
First Office Action dated Feb. 24, 2018 for Chinese Patent Application No. 201510262415.0, 17 pages including English transiation.
Second Chinese Office Action dated Oct. 19, 2018, for Chinese Patent Application No. 201510282415.0, 7 pages including English translation.

* cited by examiner

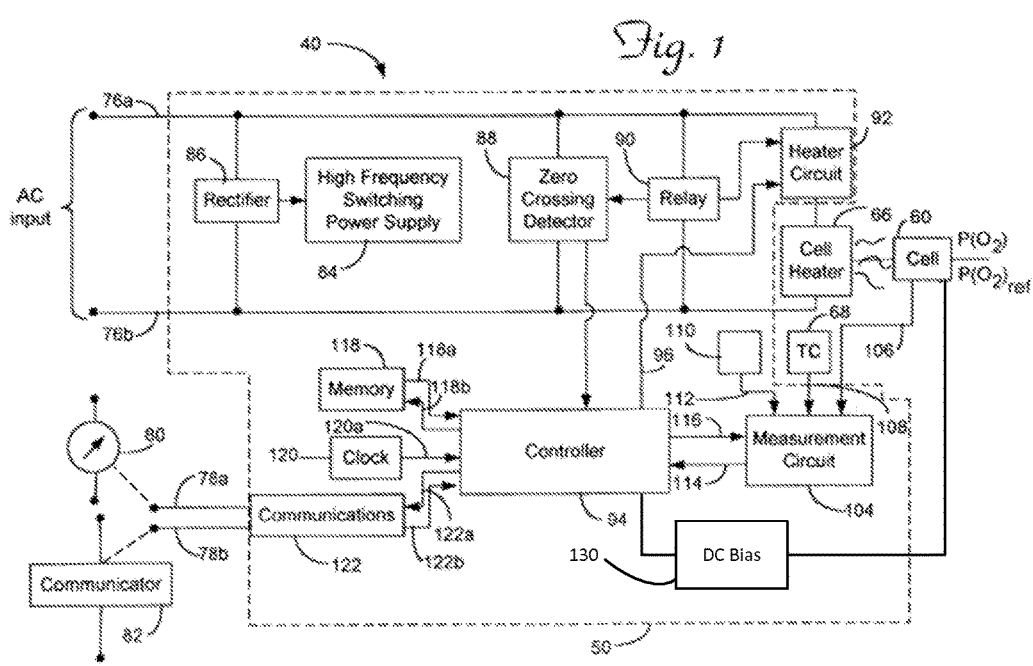

OXYGEN SENSOR WITH ELECTROCHEMICAL PROTECTION MODE

BACKGROUND

Process analytic sensors and instruments are employed in a variety of industries to measure and control gasses and liquids. Some process analytic sensors, such as oxygen sensors, utilize a heated solid electrolyte cell to measure a gas species of interest. As used herein, the term solid electrolyte cell means a quantity of the solid electrolyte, for example zirconia-yttria $((ZrO_2)_{(1-x)}(Y_2O_3)_x)$, and porous electrical contacts or electrodes connected thereto, usually made of platinum or other suitable materials.

Gas analyzers having a probe with a solid electrolyte cell to measure gaseous oxygen are well known. In one commercially available sensor (See U.S. Pat. No. 3,928,161) two porous platinum electrodes are deposited on opposite sides of the porous zirconia solid electrolyte. A common application for such analyzers is the measurement of gaseous oxygen in a flue or duct such as a smokestack. The response of the sensor to the differential oxygen concentrations with the reference electrode partial pressure fixed, e. g. air, can be calculated on the process side using the Nernst equation:

$$EMF = \left(\frac{RT}{4F}\right)\ln\left(\frac{P_{process}}{P_{ref}}\right) + C = \qquad \text{Eq. 1}$$

$$S\log\left(\frac{P_{process}}{P_{ref}}\right) + C = 0.496*T*\log\left(\frac{P_{process}}{P_{ref}}\right) + C,$$

C is a cell constant, S is a cell slope which is a function of cell temperature T, and $P_{process}$ and $P_{ref}$ are the oxygen partial pressure at a measurement and reference end, respectively, of the solid electrolyte cell. Actual solid electrolyte cells deviate from Equation 1 to some extent after aging in the combustion process.

SUMMARY

A process analytic instrument includes a measurement cell and an analyzer circuit. The measurement cell includes a solid state electrochemical oxygen sensor configured for exposure to a process gas. The analyzer circuit is coupled to the solid state electrochemical sensor to measure an electrical parameter of the solid state electrochemical sensor and provide an output indicative of oxygen in the process gas. A DC bias circuit is configured to selectably bias the solid state electrochemical oxygen sensor with a direct current when the solid state electrochemical sensor is in a reducing environment.

BRIEF DESCRIPTION OF THE DRAWINGS

FIG. 1 is a diagrammatic perspective view of a process analyzer with which embodiments of the present invention are particularly useful.

DETAILED DESCRIPTION OF ILLUSTRATIVE EMBODIMENTS

Figure 2A:
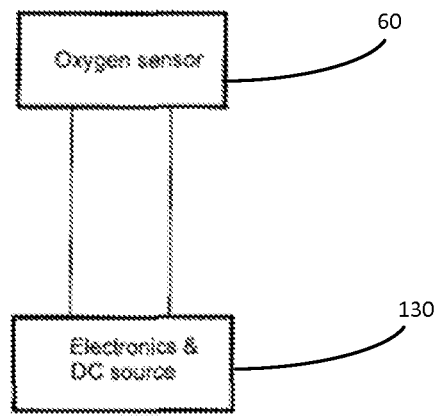
FIGS. 2A and 2B are block diagram illustrating various ways in which a bias current can be applied to an oxygen sensor in accordance with an embodiment of the present invention.

While electrochemical zirconia-based oxygen sensors are robust and can function effectively for years in a combustion environment, some particular conditions can quickly damage or otherwise degrade the sensor. The application of aggressive, especially sulfur containing, process gas at a higher temperature can abruptly shorten the life of the sensor under reducing conditions. As used herein, "reducing conditions" means atmospheric conditions in which oxidation is prevented by removal of oxygen and other oxidizing gases or vapors, and which may contain actively reducing gases such as hydrogen, carbon monoxide and gases that would oxidize in the presence of oxygen, such as hydrogen sulfide. The reduction in sensor life is believed to be due to sulfur and carbon formation as follows:

$$SO_2 + 2CO \leftarrow\rightarrow S(g) + 2CO_2 \qquad \text{Eq. 2}$$

$$2CO \leftarrow\rightarrow C + 2CO_2 \qquad \text{Eq. 3}$$

Sulfur may cause significant deactivation even at very low concentrations, due to the formation of strong metal-S bonds. Two reaction pathways are possible for sulfur poisoning: bulk or surface sulfidation, with the latter predominating. The reaction with sulfur would lead to rapid electrode deterioration. Carbon deposition on the process electrode with the following diffusion through the porous electrode film will contribute to the platinum film flaking from the zirconia ceramic surface because of the thermal expansion mismatch.

Depending on the application temperatures, a micro size diffuser or filter could be used for the protection of the cell against carbon or sulfur in the solid phase and molecular sieves such as zeolites could be considered for the potential application in carbon or sulfur oxides adsorption. In both cases, the sensor protection mode will be significantly limited due to the filter or molecular sieve's rapid degradation in the dusty combustion environment. Further, the pore size limitation in the filter will still permit very fine carbon dust or sulfur powder penetration to the process electrode surface.

Another option that was considered was to place catalyst beads in the sensor packaging before the flue gas would be reaching the process electrode film or to replace the process electrode or coat the electrode with a sulfur resistive film. In the past, sulfur tolerant composite electrodes based on oxides selected from the group of zirconium, yttrium, scandium, thorium, rare earth metals, and mixtures thereof have been studied. See for example, U.S. Pat. No. 4,702,971. More reliable sulfur-tolerant mixed conducting materials have been considered based on fluorite-type oxide ion conducting solid electrolytes, i.e. based on ceria having considerably higher ionic and electronic conductivity. Ceria-based oxides, besides being oxygen conductors, exhibit considerable electronic conduction as compared to zirconia with considerably increased electrode active surface area for the chemical redox reactions. However, none of these materials have sufficient electronic conductivity and would still require application of an effective electronic conductive collector such as platinum. This means that the sensor performance will still be highly affected by sulfur.

In accordance with an embodiment of the present invention, an oxygen sensor is provided with two modes. In an oxidizing environment (>0.1% $O_2$) the oxygen sensor will operate in a measurement mode precisely measuring oxygen concentration using the Nernst Equation. However, when the oxygen concentration in the process gas drops below a threshold, such as 0.1% $O_2$, the sensor will be switched to an Electrochemical Protection Mode (EPM) where an external bias DC voltage is applied to the sensor. In this mode, process electrode degradation is reduced or eliminated by creating an oxygen protection buffer zone over the process platinum electrode film.

FIG. 1 shows a block diagram of an exemplary analyzer circuit 50 in a solid electrolyte analyzer 40 with which embodiments of the present invention are particularly useful. Circuit 50 is energized by AC line input provided across lines 76a, 76b by a remote source. Circuit 50 controls a cell heater 66 which is arranged to heat a solid electrolyte cell 60. Cell heater 66 is typically formed of a length of nichrome wire helically wrapped around a quartz support cylinder. A thermocouple 68 or other high temperature sensing device detects the temperature of solid electrolyte cell 60, and/or of heater 66, for monitoring and feedback control. Circuit 50 monitors a cell output $V_{cell}$ from solid electrolyte cell 60 and a temperature T from thermocouple 68, and communicates a parameter indicative of $P(O_2)$ over lines 78a, 78b to a meter 80 or other suitable device, such as communicator 82.

Circuit 50, in some implementations, uses a switching power supply 84 coupled to lines 76a, 76b through a rectifier 86. Also coupled across lines 76a, 76b in parallel with rectifier 86 are a zero crossing detector 88, a relay 90, and a series combination of a heater circuit 92 with the cell heater 66. Controller 94 controls heater circuit 92 over line 96 to maintain thermocouple 68, and hence solid electrolyte cell 60, at a specified elevated temperature. Controller 94 also couples to a measurement circuit 104 over lines 114, 116. Measurement circuit 104 receives the output of solid electrolyte cell 60 over a line 106, the output of thermocouple 68 over a line 108, and the output of a local temperature sensor 110 over a line 112. These outputs are communicated to controller 94 over a line 114. The output at line 112 indicates the temperature inside an electronics housing (not shown) that houses circuit 50. Controller 94 uses the sensor 110 output as an indication of cold junction temperature to correct the raw EMF output from thermocouple 68 in calculating cell temperature T. Sensor 110 can be any suitable temperature sensor such as a thermistor.

Controller 94 also communicates with a non-volatile memory circuit 118, a clock circuit 120, and a communications module 122 over lines 118a, 118b, line 120a and lines 122a, 122b, respectively. Memory 118 holds an equation similar to EQ. 1 relating measured $V_{cell}$ and cell temperature T to oxygen content $P(O_2)$. Memory 118 also stores information indicative of a threshold at or below which controller 94 will provide the DC bias current to cell 60, via DC bias circuit 130 to thereby place cell 60 in the EPM mode.

Figure 2B:
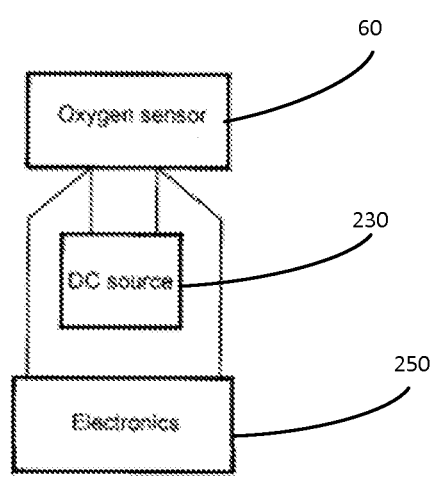

FIGS. 2A and 2B are block diagram illustrating various ways in which a bias current can be applied to an oxygen sensor in accordance with an embodiment of the present invention. FIG. 2A illustrates oxygen sensor 60 coupled to a combination electronics/DC source unit 130, such as described above with respect to FIG. 1. However, embodiments of the present invention can be applied to legacy devices where the analyzer is not used to determine whether the $O_2$ concentration is at or below the EPM threshold. Thus, in FIG. 2B, electronics 250 is coupled to oxygen sensor 60 and simply obtains oxygen measurements. If the signal from sensor 60, as measured by another device or obtained manually, indicates that the signal is below the EPM threshold, then external DC source 230 is coupled to oxygen sensor 60 to bias oxygen sensor. While the sensor is in EPM mode, oxygen measurements can still be obtained. In fact such measurements are advantageously used to determine when the oxygen concentration increases sufficiently to disengage EPM mode.

By applying a sufficient DC voltage to the electrochemical cell that is slightly higher than the cell voltage produced in the reducing conditions, an effective protection mode will be established. During such mode, the electrochemical cell (sensor) will be working as a pump transferring oxygen to the process electrode. Preliminary investigations using an approximate −1 VDC bias to the $O_2$ cell showed sufficient protection to the electrochemical cell in a reducing environment with the oxygen buffer formation close to the electrode surface and no evidence of any soot or sulfur formation.

Figure 3:
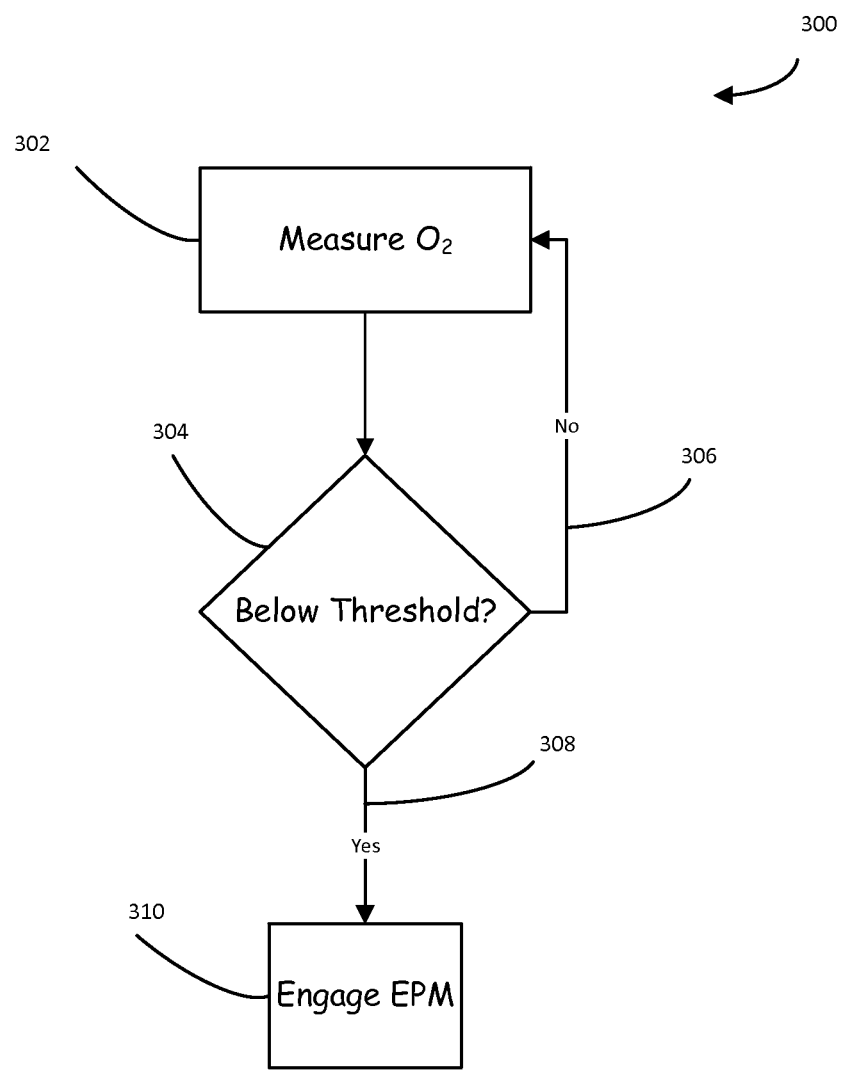
FIGS. 3 and 4 are flow diagrams methods of operating a solid state electrochemical sensor in accordance with an embodiment of the present invention.
Figure 4:
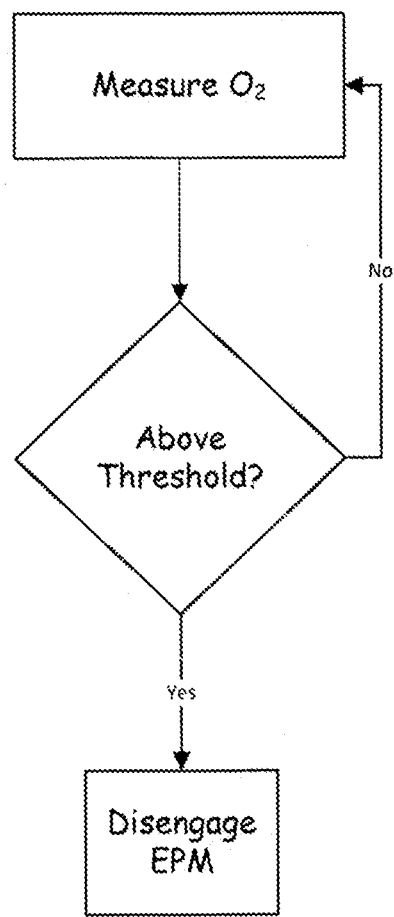

FIGS. 3 and 4 are flow diagrams of methods of operating a solid state electrochemical sensor in accordance with an embodiment of the present invention. Method 300, shown in FIG. 3, begins at block 302 where the analyzer circuitry obtains an oxygen measurement from the solid state measurement cell. At block 304, the measurement is compared with a threshold value. In one example, this value is 0.1% $O_2$, however other suitable values can be used depending on the application. Additionally, in some embodiments, the threshold may be changeable by a user depending on the application. Further still, the threshold may be based, at least in part, on the temperature of the measurement cell such that higher temperatures will engage the EPM mode at lower oxygen concentrations than lower temperatures. Further still, this temperature/concentration relationship may be adjusted by an end user or the manufacturer of the analyzer, based on the application. If the measurement is not at or below the threshold, control returns to block 302, via line 306, and method 300 cycles in normal measurement mode until the oxygen concentration drops to the threshold value. Once the oxygen concentration is at or below the threshold, control passes to block 310 via line 308 where a DC bias voltage is applied to the sensor, thereby placing the sensor in EPM mode. While in EPM mode, oxygen measurements are performed in accordance with the method shown in FIG. 4.

Although the present invention has been described with reference to preferred embodiments, workers skilled in the art will recognize that changes may be made in form and detail without departing from the spirit and scope of the invention.

What is claimed is:

1. A process analytic instrument comprising:
a measurement cell including a solid state electrochemical oxygen sensor configured for exposure to a process gas;
an analyzer circuit coupled to the solid state electrochemical sensor that measures an electrical parameter of the solid state electrochemical sensor and provides an output indicative of an oxygen level in the process gas, the analyzer circuit having a measurement mode in which the output is provided based on the oxygen level in the process gas, and a protection mode, in which a DC bias voltage is applied to the solid state electrochemical oxygen sensor, the analyzer circuit switching between the measurement mode and the protection mode based on the oxygen level being below a selected threshold; and
a DC bias circuit, coupled to the analyzer circuit, that biases the solid state electrochemical oxygen sensor with the DC bias voltage and thereby engages the analyzer circuit in the protection mode.

2. The process analytic instrument of claim 1, wherein the DC bias circuit is part of the analyzer circuit.

3. The process analytic instrument of claim 1, wherein the selected threshold corresponds to an oxygen level of 0.1% or less.

4. The process analytic instrument of claim 1, wherein the analyzer circuit causes the DC bias circuit to selectably bias the solid state electrochemical based on a comparison of the provided output to the selected threshold.

5. The process analytic instrument of claim 4, wherein the analyzer circuit provides process gas oxygen measurements while the solid state electrochemical sensor is biased with the direct current.

6. The process analytic instrument of claim 5, wherein the analyzer circuitry causes the DC bias circuit to stop biasing the solid state electrochemical sensor when the comparison indicates the oxygen level in the process gas is above the selected threshold.

7. The process analytic instrument of claim 1, wherein a DC bias voltage is higher than a voltage produced by the solid state electrochemical sensor in a reducing condition.

8. The process analytic instrument of claim 7, wherein the voltage produced by the solid state electrochemical sensor is about 1 volt.

9. The process analytic instrument of claim 1, wherein the solid state electrochemical oxygen sensor includes a platinum electrode film.

10. The process analytic instrument of claim 9, wherein an oxygen protection buffer is created proximate the platinum electrode film when the analyzer circuit is in the protection mode.

11. A process oxygen sensing instrument comprising:
a measurement cell including a solid state electrochemical oxygen sensor configured for exposure to a process gas, the solid state electrochemical oxygen sensor having an electrical characteristic that varies in response to oxygen concentration in the process gas;
a controller coupled to non-volatile memory, the non-volatile memory containing an equation relating the electrical characteristic to the oxygen concentration, the non-volatile memory also containing threshold information indicating a threshold, the controller having a first mode in which an oxygen concentration is above the threshold and a second mode in which the oxygen concentration is below the threshold;
measurement circuitry electrically interposed between the measurement cell and the controller, the measurement circuitry communicating information indicative of the electrical characteristic of the solid state electrochemical oxygen sensor to the controller;
a communication module coupled to the controller and configured to communicate a process oxygen level over external communication lines; and
a DC bias circuit, coupled to the controller and the solid state electrochemical oxygen sensor, that selectively applies a DC bias voltage to the solid state electrochemical sensor when the controller is in the second mode.

12. The process oxygen sensing instrument of claim 11, wherein the threshold corresponds to an oxygen concentration of 0.1%.

13. The process oxygen sensing instrument of claim 11, wherein the DC bias voltage is larger than a voltage produced by the sold state electrochemical oxygen sensor when the solid state electrochemical oxygen sensor is in a reducing condition.

14. The process oxygen sensing instrument of claim 11, wherein the DC bias voltage is about 1 volt.

15. The process oxygen sensing instrument of claim 11, and further comprising:
a cell heater in thermal contact with the measurement cell;
a heater circuit coupled to the controller and configured to heat the measurement cell based on a signal from the controller; and
a temperature sensor coupled to the measurement circuitry and disposed to sense a temperature of the measurement cell.

16. The process oxygen sensing instrument of claim 15, wherein the temperature sensor is a thermocouple.

17. The process oxygen sensing instrument of claim 16, and further comprising a second thermocouple coupled to the measurement circuitry.

\* \* \* \* \*

UNITED STATES PATENT AND TRADEMARK OFFICE
CERTIFICATE OF CORRECTION

PATENT NO. : 10,161,899 B2
APPLICATION NO. : 14/502490
DATED : December 25, 2018
INVENTOR(S) : Pavel Shuk and Robert F. Jantz Page 1 of 1

It is certified that error appears in the above-identified patent and that said Letters Patent is hereby corrected as shown below:

In the Specification

Column 1, Line 61: "diagram" should be "diagrams"

Column 3, Line 52: "diagram" should be "diagrams"

In the Claims

Column 5, Line 17, Claim 7: "a" should be "the"

Signed and Sealed this
Tenth Day of March, 2020

Andrei Iancu
*Director of the United States Patent and Trademark Office*